(12) United States Patent
Ribery et al.

(10) Patent No.: US 6,812,192 B2
(45) Date of Patent: Nov. 2, 2004

(54) FOAMING COSMETIC COMPOSITIONS, USES FOR CLEANSING OR MAKE-UP REMOVAL

(75) Inventors: Delphine Ribery, Levallois Perret (FR); Laure Bissey-Beugras, Levallois Perret (FR)

(73) Assignee: L'Oreal S.A., Paris (FR)

( * ) Notice: Subject to any disclaimer, the term of this patent is extended or adjusted under 35 U.S.C. 154(b) by 41 days.

(21) Appl. No.: 10/400,580

(22) Filed: Mar. 28, 2003

(65) Prior Publication Data

US 2003/0224955 A1 Dec. 4, 2003

Related U.S. Application Data

(60) Provisional application No. 60/382,564, filed on May 24, 2002.

(30) Foreign Application Priority Data

Mar. 28, 2002 (FR) .............................. 02 03929

(51) Int. Cl.$^7$ ................................. A61K 7/50
(52) U.S. Cl. ................ 510/130; 510/136; 510/158; 510/426; 510/427; 510/490; 510/492; 510/499; 424/70.1
(58) Field of Search ................. 510/130, 136, 510/158, 492, 490, 499, 426, 427; 424/70.1

(56) References Cited

U.S. PATENT DOCUMENTS

| | | | | |
|---|---|---|---|---|
| 5,858,342 A | * | 1/1999 | Giret et al. .............. | 424/70.19 |
| 5,925,603 A | * | 7/1999 | D'Angelo .................... | 510/119 |
| 5,942,477 A | * | 8/1999 | Giret et al. ................. | 510/124 |
| 5,977,037 A | * | 11/1999 | Giret et al. ................. | 510/122 |
| 5,994,280 A | * | 11/1999 | Giret et al. ................. | 510/130 |
| 6,071,541 A | | 6/2000 | Murad | |
| 6,077,816 A | | 6/2000 | Puvvada et al. | |
| 2003/0083210 A1 | * | 5/2003 | Goldberg et al. ........... | 510/130 |

FOREIGN PATENT DOCUMENTS

WO     WO 01/41729     6/2001

OTHER PUBLICATIONS

Database WPI, Section Ch, Week 199605, Derwent Publications Ltd., London, GB; AN 1996–045298, XP002229531.

Database WPI, Section Ch, Week 198829, Derwent Publications Ltd., London, GB; AN 1988–202120, XP002229532.

M.R. Porter, "Handbook of Surfactants," Blackie & Son Ltd., Glasgow and London, 1991, pp. 116–178.

* cited by examiner

*Primary Examiner*—Necholus Ogden
(74) *Attorney, Agent, or Firm*—Finnegan, Henderson, Farabow, Garrett & Dunner LLP

(57) ABSTRACT

A foaming composition for topical application, comprising at least one surfactant system comprising at least one fatty acid chosen from partially and completely neutralized fatty acids, at least one non-betaine amphoteric co-surfactant and at least one anionic co-surfactant of the sulphosuccinate type and its use in the cosmetic or dermatological fields, for example, as cleansing and/or make-up-removing products for a human keratinous material, for example, the skin.

60 Claims, No Drawings

FOAMING COSMETIC COMPOSITIONS, USES FOR CLEANSING OR MAKE-UP REMOVAL

This application claims benefit of U.S. Provisional Application No. 60/382,564, filed May 24, 2002.

Disclosed herein is a foaming composition for topical application, comprising at least one surfactant system comprising at least one fatty acid chosen from partially and completely neutralized fatty acids, at least one non-betaine amphoteric co-surfactant and at least one anionic co-surfactant of the sulphosuccinate type. Further disclosed herein is the use of the foaming composition in the cosmetic or dermatological fields, for example, as cleansing and/or make-up-removing products for a human keratinous material such as skin.

Cleansing the skin is very important for facial care. It should be as effective as possible because fatty residues such as excess sebum, residues of the cosmetic products used daily and make-up products, for example, waterproof products, accumulate in skin folds and can obstruct the pores of the skin and cause the appearance of spots.

Several classes of skin cleansing products are known, for example, foaming detergent aqueous lotions and gels, rinsable cleansing anhydrous oils and gels and foaming creams.

Rinsable anhydrous oils and gels can have a cleansing action by virtue of the oils contained in these formulations. These oils can allow the solubilization of the fatty residues and the dispersion of the make-up pigments. These products can be effective and well tolerated. They may have at least one of the following disadvantages that include but is not limited to: being heavy, not foaming, and not conferring a cooling sensation upon application, any or all of these disadvantages may be a drawback from a cosmetic point of view.

The foaming detergent aqueous lotions and gels can have a cleansing action by virtue of the surfactants which can suspend the fatty residues and the pigments of make-up products. They can be effective and pleasant to use because they can foam and they can be easily removed. However, these lotions and gels may be quite fluid, which may, for example, make their handling sometimes delicate, and it may be difficult to thicken gels while retaining good foaming properties.

Foaming creams have been prepared in an attempt to obtain good foaming performance while providing a thick composition. As used herein, the expression "foaming creams" means viscous, opaque compositions which are, for example, packaged in tubes and which comprise an aqueous medium comprising at least one surfactant chosen from, for example, fatty acid salts (soaps) and anionic, non-ionic and amphoteric synthetic surfactants, and at least one other additive such as polymers, polyols and fillers. Further, the expression "soiling residues," as used herein, means any matter found on a human keratinous material, for example, make-up residues or dirt particles.

These creams, which are intended, for example, for cleansing the skin, can produce foam when they are mixed with water. They can be used, for example, in two ways:
the first use comprises spreading the cream on hands, applying it to face and/or body and then massaging it in the presence of water in order to produce the foam directly on the face and/or the body:
the of other possible use of this type of product comprises producing the foam in the palms of the hand before applying it to the face and/or the body.
In both cases, the foam may then be rinsed off.

Among the foaming creams which are currently commercially available, some produce foams whose qualities may not yet be satisfactory, for example, as regards to the rapid initiation of foaming, the foaming power, and the creamy nature of the foam (i.e., density). Other foaming creams may, for example, become unstable over time and, for example, may be sensitive to temperature variations and to transport and storage conditions. These factors may cause macroscopic demixing, resulting in a separation into at least two phases.

A cleansing foaming cream should, for example, be resistant after several months to temperature variations and to transport and storage conditions. Indeed, during its life, the product may be exposed to temperatures which vary according to climatic, storage or transport conditions. It may also, for example, be subjected to shaking during its transportation. Further, it may also be necessary for these foaming creams to be capable of use in hot countries without any problems posed by their transportation and their preservation.

Therefore, there is still a need for a cleansing foaming cream which can be storage stable, resistant to fluctuations in temperature and transport conditions and which does not exhibit at least one of the disadvantages listed above.

The inventors have discovered, surprisingly, that it was possible to overcome at least one of the disadvantages listed above and to obtain a foaming composition provided in the form of a cream having good stability by using at least one surfactant system comprising at least one fatty acid chosen from partially and completely neutralized fatty acids, at least one non-betaine amphoteric co-surfactant, and at least one sulphosuccinate-type anionic co-surfactant.

It is thus possible to obtain an opaque composition which may have at least one of the following excellent cosmetic properties: softness and unctuousness, which can exhibit good spreading straight from the tube, produce a foam which starts rapidly, which can be creamy, dense and which can be removed very quickly upon rinsing. The composition obtained may also have, for example, good resistance over time to temperature variations and to transport conditions.

Thus, disclosed herein is a foaming composition for topical application, comprising, in a cosmetically acceptable aqueous medium, at least one surfactant system comprising:
(a) at least one fatty acid chosen from partially and completely neutralized fatty acids, wherein the at least one fatty acid is neutralized with at least one base chosen from organic and inorganic bases;
(b) at least one non-betaine amphoteric surfactant; and
(c) at least one sulphosuccinate-type anionic surfactant; provided that the weight ratio of the at least one non-betaine amphoteric surfactant to the at least one sulphosuccinate-type anionic surfactant is less than about 2:1.

Also disclosed herein is the cosmetic use of the composition as defined above, as cleansing and/or make-up-removing products for keratinous materials.

Further disclosed herein is a cosmetic method for cleansing the soiling residues of a human keratinous material, comprising applying the composition disclosed herein to said keratinous material, in the presence of water, performing a massage in order to form a foam, contacting the foam formed with the soiling residues, and removing the foam formed and the soiling residues by rinsing with water.

As used herein, the expression "a human keratinous material" means skin (body or face including eyelids and scalp) and the superficial body growths such as hair, eyelashes and eyebrows.

The at least one fatty acid disclosed herein is chosen, for example, from fatty acids comprising at least one alkyl chain chosen from saturated and unsaturated, linear and branched alkyl chains comprising from 6 to 30 carbon atoms, for example, from 12 to 22 carbon atoms.

The at least one fatty acid may, for example, be chosen from lauric acid, myristic acid, palmitic acid and stearic acid. In one embodiment, the at least one fatty acid is a mixture of lauric acid, myristic acid, palmitic acid and stearic acid.

The at least one base that may be used for partially or completely neutralizing the at least one fatty acid may, for example, be chosen from inorganic bases such as alkali metal hydroxides (such as sodium hydroxide and potassium hydroxide), alkaline-earth metal hydroxides (such as magnesium hydroxide) and aqueous ammonia, and organic bases such as triethanolamine, monoethanolamine, monoisopropanolamine, N-methylglucamine, lysine and arginine. For example, potassium hydroxide may be used.

According to one embodiment, the at least one fatty acid may be introduced into the composition in free form and then the at least one base is added, the neutralization occurring in situ.

The at least one fatty acid disclosed herein may be present, for example, in an amount ranging from about 2 to about 50% by weight, further for example, from about 5 to about 45% by weight, and even further, for example, from about 10 to about 40% by weight, relative to the total weight of the composition.

In one embodiment, the at least one fatty acid may be used, wherein the degree of neutralization may range from about 50 to about 90 mol % and further, for example, from about 55 to about 75 mol %.

The at least one sulphosuccinate-type anionic surfactant may be chosen, for example, from those corresponding to formula (I):

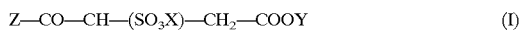

$$Z\text{—}CO\text{—}CH\text{—}(SO_3X)\text{—}CH_2\text{—}COOY \qquad (I)$$

wherein X is an ion chosen from ions derived from alkali metals and ions derived from organic amine-containing bases and, ammonium ions;

Y is chosen from X and R;

R is chosen from linear, branched and cyclic $C_6$–$C_{30}$ alkyl and alkenyl chains;

Z is chosen from groups OR, $R(OCH_2CH_2O)_n O$ and RCONHW wherein W is chosen from $(CH_2CH_2O)_{n'}$ and $(CH_2CH(CH_3)\text{—}O)_{n''}$ wherein n, n' and n", which may be identical or different, are each chosen from integers ranging from 1 to 10.

The at least one sulphosuccinate-type anionic surfactant may be chosen, for example, from oxyethylenated (3 EO) lauryl alcohol monosulphosuccinate ($C_{12}/C_{14}$ 70/30) marketed under the names SETACIN 103 SPECIAL, REWOPOL SB-FA 30 K 4 by the company Witco, the disodium salt of a $C_{12}$–$C_{14}$ alcohol hemisulphosuccinate, marketed under the name SETACIN F SPECIAL PASTE by the company Zschimmer Schwarz, the oxyethylenated (2 EO) disodium oleamidosulphosuccinate marketed under the name STANDAPOL SH 135 by the company Henkel, the oxyethylenated (5 EO) laurylamide monosulphosuccinate marketed under the name LEBON A-5000 by the company Sanyo, the oxyethylenated (10 EO) disodium salt of lauryl citrate monosulphosuccinate marketed under the name REWOPOL SB CS 50 by the company Witco, and the monoricinoleic monosulphosuccinate marketed under the name REWODERM S 1333 by the company Witco.

According to one embodiment, oxyethylenated (2 EO) disodium oleamidosulphosuccinate may be used.

The at least one sulphosuccinate-type anionic surfactant disclosed herein may be present, for example, in an amount ranging from about 0.2 to about 20% by weight, further for example, from about 1 to about 15% by weight, relative to the total weight of the composition.

The at least one non-betaine amphoteric surfactant may, for example, be chosen from amphoteric surfactants of the imidazoline type corresponding to formula (II):

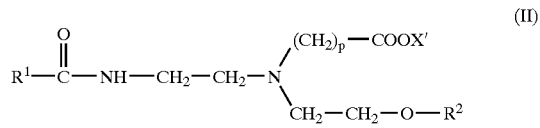

(II)

wherein:
$R^1$ is chosen from saturated and unsaturated, linear and branched $C_6$–$C_{30}$ hydrocarbon radicals;

$R^2$ is chosen from a hydrogen atom and the group —$(CH_2)_q$—COOY';

X' and Y', which may be identical or different, are each chosen from a hydrogen atom and monovalent cations, for example, metal cations, for example, alkali metal cations such as a sodium cation;

p and q, which may be identical or different, are each equal to 1 or 2.

For example, the amphoteric surfactants of formula (II) disclosed herein are chosen from those having at least one, and, for example, several, of the following characteristics:

p and q are identical;

X' and Y' are identical and, for example, are chosen from monovalent metal cations, for example, a sodium cation;

$R^1$ is chosen from alkyl radicals such as $C_5$–$C_{20}$ alkyl radicals, for example, $C_7$, $C_9$, $C_{11}$, $C_{13}$ and $C_{17}$ alkyl radicals, an unsaturated $C_{17}$ radical, and alkyl radicals of an acid $R^1$—COOH present in natural oils, such as coconut oil, coprah oil, linseed oil, wheatgerm oil and animal tallow.

For example, the imidazoline-type amphoteric surfactants may be chosen from at least one of those sold under the general trade name of MIRANOL® by the company Rhodia Chimie, and those having the following CTFA names (CTFA dictionary, 4th Edition, 1991): Sodium Caproamphoacetate, Sodium Caproamphopropionate, Sodium Capryloamphoacetate, Sodium Capryloamphopropionate, Sodium Cocoamphoacetate, Sodium Cocoamphopropionate, Sodium Isostearoamphoacetate, Sodium Isostearoamphopropionate, Sodium Lauroamphoacetate, Sodium Lauroamphopropionate, Sodium Oleoamphoacetate, Sodium Oleoamphopropionate, Sodium Stearoamphoacetate, Stearoamphopropionate, Sodium Tallowamphoacetate, and Sodium Wheatgermamphoacetate, Disodium Caproamphodiacetate, Disodium Caproamphodipropionate, Disodium Capryloamphodiacetate, Disodium Caprylo-amphodipropionate, Disodium Cocoamphodiacetate, Disodium Cocoamphodipropionate, Disodium Isostearoamphodiacetate, Disodium Isostearoamphodipropionate, Disodium Lauroamphodiacetate, Disodium Lauroamphodipropionate, Disodium Oleoamphodipropionate, Disodium Stearoamphodiacetate, Disodium Tallowamphodiacetate and Disodium Wheatgermamphodiacetate.

Sodium Cocoamphoacetate, such as the commercial product sold under the name MIRANOL ULTRA C32 by the company Rhodia Chimie, may, for example, be used.

The at least one non-betaine amphoteric surfactant disclosed herein may, for example, be present in an amount ranging from about 0.2 to about 30% by weight, and for example, from about 1 to about 20% by weight, relative to the total weight of the composition.

The weight ratio of the at least one non-betaine amphoteric surfactant to the at least one sulphosuccinate-type anionic surfactant is less than about 2:1. For example, it may range from about 0.25:1 to about 1.5:1, and, further for example, may be less than or equal to about 1.2:1.

The composition disclosed herein may further comprise at least one additional surfactant chosen from anionic surfactants other than those of the sulphosuccinate type, betaine amphoteric surfactants and nonionic surfactants.

The anionic surfactants other than those of the sulphosuccinate type may, for example, be chosen from at least one of salts, for example, alkali metal salts such as sodium salts; ammonium salts; amine salts; amino alcohol salts; and salts of alkaline-earth metals, for example salts of magnesium. Further, for example, at least one of the salts of the following types may be used: alkyl sulphates, alkyl ether sulphates, alkyl amidoether sulphates, alkyl aryl polyether sulphates, monoglyceride sulphates; alkyl sulphonates, alkyl amide sulphonates, alkyl aryl sulphonates, α-olefin sulphonates, paraffin sulphonates, alkyl sulphoacetates, acyl sarcosinates acyl glutamates, and the alkyl and acyl groups of all these compounds comprising from 6 to 24 carbon atoms and the aryl group, for example, chosen from phenyl and benzyl groups. The anionic surfactants other than those of the sulphosuccinate type may also be chosen, for example, from at least one of the esters of $C_6$–$C_{24}$ alkyl and polyglycoside carboxylic acids such as alkyl glucoside citrates, alkyl polyglycoside tartrates; alkyl sulphosuccinamates, acyl isethionates and N-acyltaurates, the alkyl and acyl group of all these compounds comprising from 12 to 20 carbon atoms. Further, for example, the anionic surfactants other than those of the sulphosuccinate type may be chosen from at least one of acyl lactylates wherein the acyl group comprises from 8 to 20 carbon atoms.

The anionic surfactants other than those of the sulphosuccinate type may also be chosen, for example, from at least one of alkyl D-galactoside uronic acids, polyoxyalkylenated ($C_6$–$C_{24}$)alkyl ether carboxylic acids, polyoxyalkylenated ($C_6$–$C_{24}$)alkyl ($C_6$–$C_{24}$)aryl ether carboxylic acids, polyoxyalkylenated ($C_6$–$C_{24}$)alkyl amidoether carboxylic acids and the salts thereof, for example, those comprising from 2 to 50 ethylene oxide groups.

The betaine amphoteric surfactants, may, for example, be chosen from at least one of ($C_8$–$C_{20}$)alkylbetaines, sulphobetaines, ($C_8$–$C_{20}$)alkylamido($C_6$–$C_8$)alkylbetaines and ($C_8$–$C_{20}$)alkylamido($C_6$–$C_8$)alkylsulphobetaines.

The additional nonionic surfactants may be chosen, for example, from at least one of compounds which are well known per se (see, for example, "Handbook of Surfactants" by M. R. PORTER, published by Blackie & Son (Glasgow and London), 1991, pp. 116–178). Thus, they may be chosen, for example, from at least one of alcohols; alphadiols ($C_1$–$C_{20}$)alkylphenols; and polyethoxylated, polypropoxylated and polyglycerolated fatty acids, comprising at least one fatty chain comprising, for example, from 8 to 18 carbon atoms, it being possible for the number of ethylene oxide and propylene oxide groups to range, for example, from 2 to 50 and it being possible for the number of glycerol groups to range, for example, from 2 to 30. The additional nonionic surfactants may also be chosen, for example, from at least one of copolymers of ethylene and propylene oxides; condensates of ethylene and propylene oxides with fatty alcohols; polyethoxylated fatty amides, for example, comprising from about 2 to about 30 mol of ethylene oxide; polyglycerolated fatty amides comprising on average about 1 to about 5 glycerol groups, for example, from about 1.5 to about 4; the ethoxylated fatty acid esters of sorbitan comprising from about 2 to about 30 mol of ethylene oxide; the fatty acid esters of sucrose; the fatty acid esters of polyethylene glycol; the ($C_6$–$C_{24}$)alkyl polyglycosides; the N—($C_6$–$C_{24}$)alkylglucamine derivatives; the amine oxides such as the ($C_{10}$–$C_{14}$)alkylamine oxides; and the N—($C_{10}$–$C_{14}$)acylaminopropylmorpholine oxides.

The quantity of the at least one additional surfactant ranges, for example, from about 0.1 to about 20% by weight, further for example, from about 0.2 to about 10% by weight, relative to the total weight of the composition.

The composition disclosed herein may be provided, for example, in the form of more or less thickened creams. Their viscosity at 25° C., measured with Rhéomat RM180 (from Rheometric Scientific) with the No. 4 rotor (set TV), a measuring system 75 and a speed gradient of 200 $s^{-1}$ and a rotor rotation time of 10 min, for example, ranges from about 1 to about 20 Pa.s, and further, for example, ranges from about 2 to about 10 Pa.s.

In one embodiment, the cosmetically acceptable aqueous medium for the foaming compositions disclosed herein may comprise, in addition to water, at least one solvent chosen from lower alcohols comprising from 1 to 6 carbon atoms, such as ethanol; polyols such as glycerine; glycols such as butylene glycol, isoprene glycol, propylene glycol, and polyethylene glycols such as PEG-8; sorbitol; sugars such as glucose, fructose, maltose, lactose, and sucrose. The quantity of the at least one solvent in the composition disclosed herein may range, for example, from about 0.5 to about 30% by weight, and further for example, from about 5 to about 20% by weight, relative to the total weight of the composition.

The composition disclosed herein may further comprise at least one thickener chosen, for example, from polymers, in a concentration ranging, for example, from about 0.05 to about 2% by weight relative to the total weight of the composition.

The at least one thickener may be chosen, for example, from:

polysaccharide biopolymers such as xanthan gum, guar gum, alginates, and modified celluloses;

synthetic polymers such as polyacrylics such as CARBOPOL 980 marketed by the company GOODRICH, acrylate/acrylonitrile copolymers such as HYPAN SS201 marketed by the company KINGSTON; and inorganic thickeners such as smectites, modified hectorites and non-modified hectorites such as the products BENTONE marketed by the company RHEOX, the products LAPONITE marketed by the company SOUTHERN CLAY PRODUCTS, the products VEEGUM HS marketed by the company R. T. VANDERBILT.

The composition disclosed herein may also comprise at least one adjuvant chosen from those customarily used in the field of foaming cleansing agents such as polyquaternium-type cationic polymers which may impart softness and unctuousness to the foaming cream. The polyquaternium-type cationic polymers may, for example, be chosen from the following polymers:

Polyquaternium 5 such as the product MERQUAT 5 marketed by the company CALGON;

Polyquaternium 6 such as the product SALCARE SC 30 marketed by the company CIBA, and the product MERQUAT 100 marketed by the company CALGON;

Polyquaternium 7 such as the products MERQUAT S, MERQUAT 2200 and MERQUAT 550 marketed by the company CALGON, and the product SALCARE SC 10 marketed by the company CIBA;

Polyquaternium 10 such as the product Polymer JR400 marketed by the company AMERCHOL;

Polyquaternium 11 such as the products GAFQUAT 755, GAFQUAT 755N and GAFQUAT 734 marketed by the company ISP;

Polyquaternium 15 such as the product ROHAGIT KF 720 F marketed by the company ROHM;

Polyquaternium 16 such as the products LUVIQUAT FC905, LUVIQUAT FC370, LUVIQUAT HM552 and LUVIQUAT FC550 marketed by the company BASF;

Polyquaternium 22 such as the product MERQUAT 280 marketed by the company CALGON;

Polyquaternium 28 such as the product STYLEZE CC10 marketed by the company ISP;

Polyquaternium 39 such as the product MERQUAT PLUS 3330 marketed by the company CALGON;

Polyquaternium 44 such as the product LUVIQUAT CARE marketed by the company BASF;

Polyquaternium 46 such as the product LUVIQUAT HOLD marketed by the company BASF; and Polyquaternium 47 such as the product MERQUAT 2001 marketed by the company CALGON.

It is also possible to use, as the polyquaternium-type cationic polymer, cationic guars such as the product JAGUAR marketed by the company RHODIA.

In addition, the composition disclosed herein may also comprise at least one adjuvant chosen from those customarily used in the cosmetic field, such as oils, active agents, perfumes, preservatives, sequestrants (EDTA), pigments, pearlescent agents, inorganic and organic fillers such as talc, kaolin, silica and polyethylene powders, and soluble colourants. The amount of the at least one adjuvant is that conventionally used in the field considered, and may, for example, range from about 0.01 to about 20% by weight, of the total weight of the composition. The at least one adjuvant and its concentration should be such that they do not modify the property sought for the composition disclosed herein.

For example, the oils may be chosen from at least one of oils of plant origin (such as jojoba, avocado, sesame, sunflower, maize, soybean, safflower, grape seed), mineral oils (such as petroleum jelly, optionally hydrogenated isoparaffins), synthetic oils (such as isopropyl myristate, cetearyl octanoate, polyisobutylene, ethylhexyl palmitate, alkyl benzoates), volatile silicone oils, non-volatile silicone oils such as polydimethylsiloxanes (PDMS) and cyclodimethylsiloxanes and cyclomethicones, and fluorinated oils and fluorosilicone oils. The quantity of the oils should not modify the property sought for the composition disclosed herein. According to one embodiment, the oil is at or below about 15% by weight and may be, for example, at or below about 10% by weight relative to the total weight of the composition, and it may, for example, range from about 0.1 to about 5% by weight and even further, for example, from about 0.1 to about 3% by weight, relative to the total weight of the composition.

The active agents are chosen, for example, from at least one of sunscreens; desquamatory agents; moisturizing agents; depigmenting agents; propigmenting agents; alpha-hydroxy acids; antibacterial agents; anti-free radical agents; antipollutants; anti-inflammatory agents; retinoids; algal, fungal, plant, yeast and bacterial extracts; hydrolysed proteins, partially hydrolysed proteins, non-hydrolysed proteins; enzymes, hormones, vitamins and their derivatives, flavonoids and isoflavones.

Also disclosed herein is the cosmetic use of the composition as defined above, as cleansing and/or make-up-removing product for a human keratinous material, for example, the skin.

Further disclosed herein is a cosmetic method for cleansing the soiling residues of a human keratinous material, for example, the skin, comprising applying the composition disclosed herein to said keratinous material in the presence of water, performing a massage in order to form a foam, contacting the foam with the soiling residues, and removing the foam formed and the soiling residues by rinsing with water.

The examples which follow serve to illustrate the embodiments disclosed herein without, however, being of a limiting nature. The quantities indicated are in % by weight unless otherwise stated, and the names of the compounds are chemical names or CTFA names (International Cosmetic Ingredient Dictionary and Handbook) depending on individual cases.

| Composition | Comparative Example 1 | Comparative Example 2 | Example 3 (According to this disclosure) | Example 4 (According to this disclosure) |
| --- | --- | --- | --- | --- |
| Palmitic acid | 10.20 g | 10.20 g | 10.20 g | 10.20 g |
| Myristic acid | 10.15 g | 10.15 g | 10.15 g | 10.15 g |
| Lauric acid | 2.50 g | 2.50 g | 2.50 g | 2.50 g |
| Stearic acid | 2.65 g | 2.65 g | 2.65 g | 2.65 g |
| Potassium hydroxide | 3.66 g | 3.66 g | 3.66 g | 3.66 g |
| Disodium Oleoamido PEG-2 Sulphosuccinate | — | 2.00 g | 3.00 g | 4.00 g |
| Sodium Cocoamphoacetate | 6.00 g | 4.00 g | 3.00 g | 2.00 g |
| PEG-7 Glyceryl Cocoate | 2.00 g | 2.00 g | 2.00 g | 2.00 g |
| Glycerine | 1.00 g | 1.00 g | 1.00 g | 1.00 g |
| Ceteareth-60 myristyl glycol | 0.50 g | 0.50 g | 0.50 g | 0.50 g |
| Electrolyte | qs | qs | qs | qs |
| Preservatives | qs | qs | qs | qs |

-continued

| Composition | Comparative Example 1 | Comparative Example 2 | Example 3 (According to this disclosure) | Example 4 (According to this disclosure) |
|---|---|---|---|---|
| Sequestrant | qs | qs | qs | qs |
| Antioxidant | qs | qs | qs | qs |
| Perfume | qs | qs | qs | qs |
| Water | qs 100 g | qs 100 g | qs 100 g | qs 100 g |

The creams of Examples 1 to 4 were prepared according to the following procedure:

The water, the fatty acids (palmitic, lauric, stearic and myristic), the glycerine, the PEG-7 glyceryl cocoate, the ceteareth-60 myristyl glycol, the preservatives, the sequestrant and the antioxidant were added to a manufacturing tank, and the tank was stirred and heated to 75° C. (presence of two phases). At 750° C., disodium oleamido PEG-2 sulphosuccinate and sodium cocoamphoacetate were added, being careful with the aeration, under moderate stirring for 10 minutes at 75° C. (the cream became smooth and had a single phase).

The mixture was cooled under vacuum at 55° C. and the perfume was added and the mixture was stirred, still under vacuum.

At 50° C., the potassium hydroxide was added (95% of the total quantity to be added); the mixture was stirred for an additional 30 minutes, still under vacuum. It was cooled to 25° C., while stirring under vacuum in order to avoid aerating the product.

Viscosity at 25° C. was determined by means of the Rheomat RM180 (from Rheometric Scientific) with the No. 4 rotor (set TV), a measuring system 75 and a speed gradient of 200 s$^{-1}$ and a rotor rotation time of 10 min.

Test of Stability in the Certomat:

A Certomat® HR type apparatus provided by B. Braun Biotech International was used.

About 50 g of each formulation to be tested was removed and placed in a 100 ml glass tablet container. Each tablet container was placed in a water bath heated to 30° C. They were arranged on a tray which oscillated at 150 rpm. The oscillations of the tray simulated transport of the products.

The instability observed using this method was a phase separation, i.e., a liquid phase at the bottom of the tablet container more or less clear but not pearlescent; a pearlescent intermediate phase; and a surface phase that was slightly less pearlescent.

The appearance or otherwise of the phase separation phenomenon was observed after a period of 30 days.

The results of the tests are indicated in the following table:

| Composition | Comparative Example 1 | Comparative Example 2 | Example 3 (According to this disclosure) | Example 4 (According to this disclosure) |
|---|---|---|---|---|
| Viscosity at 25° C. in Pa.s | 9.0 | 5.7 | 4.5 | 5.7 |
| Stability in the Certomat after 30 days | Unstable Observation of a phase separation after 24 hours which was maintained after 30 days | Unstable Observation of a phase separation after 24 hours which was maintained after 30 days | Stable | Stable |

The results of the stability tests show that:

compositions 3 and 4 according to this disclosure comprising the combination of co-surfactants Sodium Cocoamphoacetate/Disodium Oleoamido PEG-2 Sulphosuccinate in a weight ratio of less than 2:1 (i.e. 1:1 and 2:4 respectively) were stable after 30 days unlike composition 1 (not forming part of this disclosure) comprising only the co-surfactant Sodium Cocoamphoacetate, and unlike composition 2 (not forming part of this disclosure) comprising the combination of co-surfactants Disodium Oleoamido PEG-2 Sulphosuccinate/Sodium Cocoamphoacetate in a weight ratio equal to 2:1.

EXAMPLES 5 TO 7

| Composition | Example 5 According to this disclosure | Example 6 According to this disclosure | Comparative Example 7 |
|---|---|---|---|
| Palmitic acid | 10.64 g | 10.20 g | 9.76 g |
| Myristic acid | 7.68 g | 10.15 g | 10.12 g |
| Lauric acid | 5.00 g | 2.50 g | 2.5 g |
| Stearic acid | 3.18 g | 2.65 g | 2.12 g |
| Potassium hydroxide | 3.96 g | 3.66 g | 3.66 g |
| Disodium Oleoamido PEG-2 Sulphosuccinate | 2.00 g | 2.00 g | 3.40 g |
| Sodium Cocoamphoacetate | 2.00 g | 2.00 g | — |
| PEG-7 Glyceryl Cocoate | 2.00 g | 2.00 g | 2.00 g |
| Glycerine | 1.00 g | 1.00 g | 1.00 g |
| Ceteareth-60 myristyl glycol | 0.50 g | 0.50 g | 0.50 g |

-continued

| Composition | Example 5 According to this disclosure | Example 6 According to this disclosure | Comparative Example 7 |
|---|---|---|---|
| Electrolyte | qs | qs | — |
| Preservatives | qs | qs | qs |
| Sequestrant | qs | qs | qs |
| Antioxidant | qs | qs | qs |
| Perfume | qs | qs | qs |
| Water | qs 100 g | qs 100 g | qs 100 g |
| Viscosity at 25° C. in Pa.s | 4.0 | 6.6 | 6.9 |

The creams of Examples 5 to 7 were prepared according to the same procedure as the preceding Examples 1 to 4. Their viscosity at 25° C. was determined by means of the Rhéomat RM180 (from Rheometric Scientific) with the No. 4 rotor (set TV), a measuring system 75 and a speed gradient of 200 $s^{-1}$ and a rotor rotation time of 10 min.

Sensory Performance:

The foam qualities of the compositions of Examples 5, 6 and 7 were evaluated by a panel of 7 people according to the protocol described below:

Before any use of the products, the hands were washed with soap and then suitably rinsed.

The following steps were then carried out:

the hands were wetted by passing them under running water thermostated at 38° C. with a flow rate of 8 l/min, 2 g of product was placed in the hollow of one of the hands, 3 ml of the same water was added and was worked the product for 15 seconds, the foam quality criteria of the test was evaluated, and the hands were rinsed under the same running water.

The following criteria were evaluated and were noted on a scale of 0 to 10.

Initiation of the foam: the quicker the initiation, the higher the score awarded.

The quantity: foaming power; the greater the amount of foam produced in the hands by the product, the higher the score awarded.

Creamy sensation: the greater the creamy sensation, the higher the score awarded.

The mean sensory results for each of the criteria are presented in the following table:

| Quality of the foam | Example 5 According to this disclosure | Example 6 According to this disclosure | Comparative Example 7 |
|---|---|---|---|
| Initiation of the foam | 6.1 | 5.8 | 4.5 |
| Quantity (foaming power) | 7.5 | 6.7 | 5.0 |
| Creamy sensation (density) | 9.0 | 8.5 | 7.3 |

The results of the sensory tests show that compositions 5 and 6 according to this disclosure comprising the combination of co-surfactants Disodium Oleoamido PEG-2 Sulphosuccinate/Sodium Cocoamphoacetate produced better quality foams than composition 7 (not forming part this disclosure) comprising only the co-surfactant Disodium Oleoamido PEG-2 Sulphosuccinate.

EXAMPLES 8 AND 9

The creams of Examples 8 and 9 were prepared according to the same procedure as the preceding Examples 1 to 4. Their viscosity at 25° C. was determined by means of the Rhéomat RM180 (from Rheometric Scientific) with the No. 4 rotor (set TV), a measuring system 75 and a speed gradient of 200 $s^{-1}$ and a rotor rotation time of 10 min.

| Composition | Example 8 | Example 9 |
|---|---|---|
| Palmitic acid | 10.64 g | 10.64 g |
| Myristic acid | 7.68 g | 7.68 g |
| Stearic acid | 3.18 g | 3.18 g |
| Lauric acid | 5.00 g | 5.00 g |
| Potassium hydroxide | 3.96 g | 3.96 g |
| Disodium Oleoamido PEG-2 Sulphosuccinate | 4.00 g | 3.00 g |
| Sodium Cocoamphoacetate | 2.00 g | 2.00 g |
| PEG-7 Glyceryl Cocoate | 2.00 g | 2.00 g |
| Glycerine | 1.00 g | 1.00 g |
| Ceteareth-60 myristyl glycol | 0.50 g | 0.50 g |
| Electrolyte | qs | qs |
| Preservative | qs | qs |
| Sequestrant | qs | qs |
| Antioxidant | qs | qs |
| Perfume | qs | qs |
| Water | qs 100 g | qs 100 g |
| Viscosity at 25° C. in Pa.s | 4.0 | 4.0 |

What is claimed is:

1. A foaming composition for topical application, comprising, in a cosmetically acceptable aqueous medium, at least one surfactant system comprising:

(a) at least one fatty acid chosen from partially and completely neutralized fatty acids, wherein the at least one fatty acid is neutralized with at least one base;

(b) at least one non-betaine amphoteric surfactant; and (c) at least one sulphosuccinate-type anionic surfactant; provided that the weight ratio of the at least one non-betaine amphoteric surfactant to the at least one sulphosuccinate-type anionic surfactant is less than about 2:1.

2. The composition according to claim 1, wherein the at least one base is chosen from organic bases.

3. The composition according to claim 1, wherein the at least one base is chosen from inorganic bases.

4. The composition according to claim 1, wherein the at least one fatty acid is chosen from carboxylic acids comprising at least one alkyl chain chosen from saturated and unsaturated, linear and branched alkyl chains comprising from 6 to 30 carbon atoms.

5. The composition according to claim 4, wherein the at least one fatty acid is chosen from carboxylic acids comprising at least one alkyl chain chosen from saturated and unsaturated, linear and branched alkyl chains comprising from 12 to 22 carbon atoms.

6. The composition according to claim 4, wherein the at least one fatty acid is chosen from lauric acid, myristic acid, palmitic acid, and stearic acid.

7. The composition according to claim 6, wherein the at least one fatty acid is a mixture of fatty acids comprising lauric acid, myristic acid, palmitic acid and stearic acid.

8. The composition according to claim 1, wherein the inorganic bases are chosen from at least one of alkali metal hydroxides, alkaline-earth metal hydroxides and ammonium hydroxide.

9. The composition according to claim 1, wherein the organic bases are chosen from at least one of amines and alkanolamines.

10. The composition according to claim 1, wherein the at least one base is potassium hydroxide.

11. The composition according to claim 1, wherein the at least one fatty acid is present in an amount ranging from about 2 to about 50% by weight, relative to the total weight of the composition.

12. The composition according to claim 11, wherein the at least one fatty acid is present in an amount ranging from about 5 to about 45% by weight, relative to the total weight of the composition.

13. The composition according to claim 12, wherein the at least one fatty acid is present in an amount ranging from about 10 to about 40% by weight, relative to the total weight of the composition.

14. The composition according to claim 1, wherein the degree of neutralization of the at least one fatty acid ranges from about 50 to about 90 mol %.

15. The composition according to claim 14, wherein the degree of neutralization of the at least one fatty acid ranges from about 55 to about 75 mol %.

16. The composition according to claim 1, wherein the at least one sulphosuccinate-type anionic surfactant is chosen from those corresponding to formula (I):

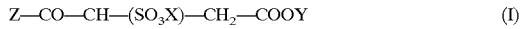

Z—CO—CH—(SO$_3$X)—CH$_2$—COOY  (I)

wherein X is an ion chosen from ions derived from alkali metal and ions derived from organic amine-containing bases and an ammonium ion;

Y is chosen from X and R;

R is chosen from linear, branched and cyclic C$_6$–C$_{30}$ alkyl and alkenyl chains;

Z is chosen from groups OR, R(OCH$_2$CH$_2$O)$_n$O and RCONHW, wherein W is chosen from (CH$_2$CH$_2$O)$_{n'}$ and (CH$_2$CH(CH$_3$)—O)$_{n''}$, wherein n, n' and n", which may be identical or different, are each chosen from integers ranging from 1 to 10.

17. The composition according to claim 16, wherein the at least one sulphosuccinate-type anionic surfactant is chosen from:

oxyethylenated (3 EO) lauryl alcohol monosulphosuccinate (C$_{12}$/C$_{14}$ 70/30), disodium salt of a C$_{12}$–C$_{14}$ alcohol hemisulphosuccinate, oxyethylenated (2 EO) disodium oleamidosulphosuccinate, oxyethylenated (5 EO) laurylamide monosulphosuccinate, oxyethylenated (10 EO) disodium salt of lauryl citrate monosulphosuccinate, and monoricinoleic monosulphosuccinate.

18. The composition according to claim 17, wherein the at least one sulphosuccinate-type anionic surfactant is oxyethylenated (2 EO) disodium oleamidosulphosuccinate.

19. The composition according to claim 1, wherein the at least one sulphosuccinate-type anionic surfactant is present in an amount ranging from about 0.2 to about 20% by weight, relative to the total weight of the composition.

20. The composition according to claim 19, wherein the at least one sulphosuccinate-type anionic surfactant is present in an amount ranging from about 1 to about 15% by weight, relative to the total weight of the composition.

21. The composition according to claim 1, wherein the at least one non-betaine amphoteric surfactant is chosen from amphoteric surfactants of the imidazoline type corresponding to formula (II):

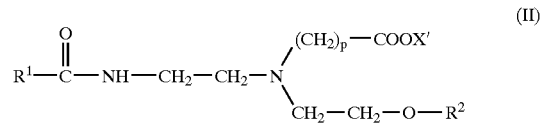

wherein:

R$^1$ is chosen from saturated and unsaturated, linear and branched C$_6$–C$_{30}$ hydrocarbon radicals;

R$^2$ is chosen from a hydrogen atom and the group —(CH$_2$)$_q$—COOY';

X' and Y', which may be identical or different, are each chosen from a hydrogen atom and monovalent cations;

p and q, which may be identical or different, are each equal to 1 or 2.

22. The composition according to claim 21, wherein, in defining X' and Y', the monovalent cations are chosen from metal cations.

23. The composition according to claim 22, wherein the metal cations are chosen from alkali metal cations.

24. The composition according to claim 23, wherein the alkali metal cations comprises sodium cations.

25. The composition according to claim 21, wherein the imidazoline type amphoteric surfactants are chosen from:

Sodium Caproamphoacetate, Sodium Caproamphopropionate, Sodium Capryloamphoacetate, Sodium Capryloamphopropionate, Sodium Cocoamphoacetate, Sodium Cocoamphopropionate, Sodium Isostearoamphoacetate, Sodium Isostearoamphopropionate, Sodium Lauroamphoacetate, Sodium Lauroamphopropionate, Sodium Oleoamphoacetate, Sodium Oleoamphopropionate, Sodium Stearoamphoacetate, Stearoamphopropionate, Sodium Tallowamphoacetate, Sodium Wheatgermamphoacetate, Disodium Caproamphodiacetate, Disodium Caproamphodipropionate, Disodium Capryloamphodiacetate, Disodium Capryloamphodipropionate, Disodium Cocoamphodiacetate, Disodium Cocoamphodipropionate, Disodium Isostearoamphodiacetate, Disodium Isostearoamphodipropionate, Disodium Lauroamphodiacetate, Disodium Lauroamphodipropionate, Disodium Oleoamphodipropionate, Disodium Stearoamphodiacetate, Disodium Tallowamphodiacetate and Disodium Wheatgermamphodiacetate.

26. The composition according to claim 25, wherein the at least one non-betaine amphoteric surfactant comprises Sodium Cocoamphoacetate.

27. The composition according to claim 1, wherein the at least one non-betaine amphoteric surfactant is present in an amount ranging from about 0.2 to about 30% by weight, relative to the total weight of the composition.

28. The composition according to claim 27, wherein the at least one non-betaine amphoteric surfactant is present in an amount ranging from about 1 to about 20% by weight, relative to the total weight of the composition.

29. The composition according to claim 1, wherein the weight ratio of the at least one non-betaine amphoteric surfactant to the at least one sulphosuccinate-type anionic surfactant ranges from about 0.25:1 to about 1.5:1.

30. The composition according to claim 29, wherein the weight ratio of the at least one non-betaine amphoteric surfactant to the at least one sulphosuccinate-type anionic surfactant is less than or equal to about 1.2:1.

31. The composition according to claim 1, further comprising at least one additional surfactant chosen from anionic surfactants other than those of the sulphosuccinate type, betaine amphoteric surfactants and nonionic surfactants.

32. The composition according to claim 31, wherein the at least one additional surfactant is present in an amount ranging from about 0.1 to about 20% by weight, relative to the total weight of the composition.

33. The composition according to claim 32, wherein the at least one additional surfactant is present in an amount ranging from about 0.2 to about 10% by weight, relative to the total weight of the composition.

34. The composition according to claim 1, wherein the composition is provided in the form of a cream.

35. The composition according to claim 1, wherein the viscosity of the composition at 25° C., in the Rhéomat RM180 with the No. 4 rotor (set TV), a measuring system 75 and a speed gradient of 200 s$^{-1}$ and a rotor rotation time of 10 min, ranges from about 1 to about 20 Pa.s.

36. The composition according to claim 35, wherein the viscosity ranges from about 2 to about 10 Pa.s.

37. The composition according to claim 1, wherein the cosmetically acceptable aqueous medium comprises at least one solvent chosen from lower alcohols, polyols, and sugars.

38. The composition according to claim 1, further comprising at least one thickening agent.

39. The composition according to claim 1, further comprising at least one polyquaternium-type cationic polymer.

40. The composition according to claim 1, further comprising at least one adjuvant chosen from oils, active agents, perfumes, preservatives, sequestrants, pigments, pearlescent agents, inorganic and organic fillers, and soluble colourants.

41. The composition according to claim 40, wherein the inorganic and organic fillers are chosen from at least one of talc, kaolin, silica, and polyethylene powders.

42. The composition according to claim 40, wherein the active agents are chosen from sunscreens; desquamatory agents; moisturizing agents; depigmenting agents; propigmenting agents; alpha-hydroxy acids; antibacterial agents; anti-free radical agents; antipollutants; anti-inflammatory agents; retinoids; algal, fungal, plant, yeast and bacterial extracts; hydrolysed, partially hydrolysed, and non-hydrolysed proteins; enzymes, hormones, vitamins and their derivatives, flavonoids and isoflavones, and mixtures thereof.

43. A cosmetic process for cleansing and/or make-up-removing comprising applying to a human keratinous material a cosmetic composition comprising, in a cosmetically acceptable aqueous medium, at least one surfactant system comprising:
   (a) at least one fatty acid chosen from partially and completely neutralized fatty acids, wherein the at least one fatty acid is neutralized with at least one base;
   (b) at least one non-betaine amphoteric surfactant; and
   (c) at least one sulphosuccinate-type anionic surfactant;
provided that the weight ratio of the at least one non-betaine amphoteric surfactant to the at least one sulphosuccinate-type anionic surfactant is less than about 2:1.

44. The process according to claim 43, wherein the at least one base is chosen from organic bases.

45. The process according to claim 43, wherein the at least one base is chosen from inorganic bases.

46. The process according to claim 43, wherein the human keratinous material is skin.

47. A cleansing and/or make-up-removing composition comprising, in a cosmetically acceptable aqueous medium, at least one surfactant system comprising:
   (a) at least one fatty acid chosen from partially and completely neutralized fatty acids, wherein the at least one fatty acid is neutralized with at least one base;
   (b) at least one non-betaine amphoteric surfactant; and
   (c) at least one sulphosuccinate-type anionic surfactant;
provided that the weight ratio of the at least one non-betaine amphoteric surfactant to the at least one sulphosuccinate-type anionic surfactant is less than about 2:1;
wherein the composition is effective in cleansing and/or make-up-removing.

48. The composition according to claim 47, wherein the at least one base is chosen from organic bases.

49. The composition according to claim 47, wherein the at least one base is chosen from inorganic bases.

50. A process for cleansing the soiling residues of a human keratinous material, comprising:
   forming a foam, in the presence of water, with a cosmetic composition, in a cosmetically acceptable aqueous medium, comprising at least one surfactant system comprising:
      (a) at least one fatty acid chosen from partially and completely neutralized fatty acids, wherein the at least one fatty acid is neutralized with at least one base;
      (b) at least one non-betaine amphoteric surfactant; and
      (c) at least one sulphosuccinate-type anionic surfactant;
      provided that the weight ratio of the at least one non-betaine amphoteric surfactant to the at least one sulphosuccinate-type anionic surfactant is less than about 2:1;
   applying the foam formed to a human keratinous material;
   removing the foam formed and the soiling residues by rinsing with water.

51. The process according to claim 50, wherein the at least one base is chosen from organic bases.

52. The process according to claim 50, wherein the at least one base is chosen from inorganic bases.

53. The process according to claim 50, wherein the human keratinous material is skin.

54. A process for cleansing the soiling residues of a human keratinous material, comprising
   applying to the keratinous material, in the presence of water, a cosmetic composition, in a cosmetically acceptable aqueous medium, at least one surfactant system comprising:
      (a) at least one fatty acid chosen from partially and completely neutralized fatty acids, wherein the at least one fatty acid is neutralized with at least one base;
      (b) at least one non-betaine amphoteric surfactant; and
      (c) at least one sulphosuccinate-type anionic surfactant;
      provided that the weight ratio of the at least one non-betaine amphoteric surfactant to the at least one sulphosuccinate-type anionic surfactant is less than about 2:1;
   performing a massage of the keratinous material with the cosmetic composition in order to form a foam, and removing the foam formed and the soiling residues by rinsing with water.

55. The process according to claim 54, wherein the at least one base is chosen from organic bases.

56. The process according to claim 54, wherein the at least one base is chosen from inorganic bases.

57. The process according to claim 54, wherein the human keratinous material is skin.

58. A process for manufacturing a cosmetic composition, comprising including in the cosmetic composition at least one surfactant system comprising:

(a) at least one fatty acid chosen from partially and completely neutralized fatty acids, wherein the at least one fatty acid is neutralized with at least one base;

(b) at least one non-betaine amphoteric surfactant; and (c) at least one sulphosuccinate-type anionic surfactant;

provided that the weight ratio of the at least one non-betaine amphoteric surfactant to the at least one sulphosuccinate-type anionic surfactant is less than about 2:1.

59. The process according to claim 58, wherein the at least one base is chosen from organic bases.

60. The process according to claim 58, wherein the at least one base is chosen from inorganic bases.

* * * * *